United States Patent
Ando et al.

(10) Patent No.: US 7,556,968 B2
(45) Date of Patent: Jul. 7, 2009

(54) SCANNING PROBE MICROSCOPE AND MOLECULAR STRUCTURE CHANGE OBSERVATION METHOD

(75) Inventors: Toshio Ando, Kanazawa (JP); Yoshiaki Hayashi, Ome (JP)

(73) Assignees: Kanazawa University Kanazawa-shi, JPX; Olympus Corporation, Tokyo (JP)

( * ) Notice: Subject to any disclaimer, the term of this patent is extended or adjusted under 35 U.S.C. 154(b) by 653 days.

(21) Appl. No.: 11/168,696

(22) Filed: Jun. 28, 2005

(65) Prior Publication Data

US 2005/0247874 A1 Nov. 10, 2005

Related U.S. Application Data

(63) Continuation of application No. PCT/JP2004/000110, filed on Jan. 9, 2004.

(30) Foreign Application Priority Data

| Jan. 9, 2003 | (JP) | ............................. 2003-003668 |
| Feb. 20, 2003 | (JP) | ............................. 2003-043065 |
| Oct. 24, 2003 | (JP) | ............................. 2003-365072 |

(51) Int. Cl.
*G01N 21/01* (2006.01)
*G01N 23/00* (2006.01)

(52) U.S. Cl. .................... 436/165; 436/164; 422/82.05; 73/105; 250/234; 250/306; 359/368

(58) Field of Classification Search ................ 436/164, 436/165; 422/82.05; 73/105; 250/234, 306; 310/323.02, 328, 330–332; 359/368
See application file for complete search history.

(56) References Cited

U.S. PATENT DOCUMENTS

| 5,912,461 | A | * | 6/1999 | Ando et al. .................. 250/306 |
| 6,021,665 | A | * | 2/2000 | Hayashi et al. ............... 73/105 |
| 6,118,121 | A | * | 9/2000 | Ando et al. .................. 250/306 |
| 6,617,761 | B2 | * | 9/2003 | Ando et al. .................. 310/328 |
| 6,809,306 | B2 | * | 10/2004 | Ando et al. ............... 250/201.3 |

FOREIGN PATENT DOCUMENTS

| JP | 7-43372 A | 2/1995 |
| JP | 10-123427 A | 5/1998 |
| JP | 10-142238 A | 5/1998 |
| JP | 10-227738 A | 8/1998 |

OTHER PUBLICATIONS

Ando et al. PNAS, vol. 98, No. 22, Oct. 23, 2001, pp. 12468-12472.*
Y. Hayashi et al; Instrumentation of a Analyzer for Single Cell's Response to Bio-Molecular and Mechanical Stimulation; "The Japan Society of Mechanical Engineers"; 1999; pp. 45-46.
English translation of Written Opinion of the International Searching Authority (Form PCT/ISA/237) issued in International Application No. PCT/JP2004/000110 filed Jan. 9, 2004.

* cited by examiner

*Primary Examiner*—Maureen M Wallenhorst
(74) *Attorney, Agent, or Firm*—Frishauf, Holtz, Goodman & Chick, P.C.

(57) ABSTRACT

A scanning probe microscope includes a cantilever, a scanning mechanism which relatively scans the cantilever and a sample which exist in liquid, and an application mechanism which applies photolytic light to a caged compound existing in the liquid or the sample.

17 Claims, 8 Drawing Sheets

SCANNING PROBE MICROSCOPE AND MOLECULAR STRUCTURE CHANGE OBSERVATION METHOD

CROSS REFERENCE TO RELATED APPLICATIONS

This is a Continuation Application of PCT Application No. PCT/JP2004/000110, filed Jan. 9, 2004, which was published under PCT Article 21(2) in Japanese.

This application is based upon and claims the benefit of priority from prior Japanese Patent Applications No. 2003-003668, filed Jan. 9, 2003; No. 2003-043065, filed Feb. 20, 2003; and No. 2003-365072, filed Oct. 24, 2003, the entire contents of all of which are incorporated herein by reference.

BACKGROUND OF THE INVENTION

1. Field of the Invention

The present invention relates to a scanning probe microscope and, more preferably, to a scanning probe microscope that is suitable for the observation of the molecular-level reaction of a biological molecule, i.e., a morphological or structural change. The present invention also relates to a molecular structure change observation method using the scanning probe microscope.

2. Description of the Related Art

A scanning probe microscope (SPM) is a generic name for devices which obtain information on a sample by mechanically scanning a probe, and includes, for example, a scanning tunneling microscope (STM), an atomic force microscope (AFM), a scanning magnetic force microscope (MFM), a scanning capacitance microscope (SCaM), a scanning near-field optical microscope (SNOM), and a scanning thermal microscope (SThM).

Recently a nanoindentator, designed to check hardness and other property of a sample by pressing a diamond probe against the sample surface to make an indentation and analyzing how the indentation is formed, has been regarded as one of SPMs, and SPM has become widely used with the above various kinds of microscopic method.

SPM can obtain surface information on a desired sample region through a probe by relatively raster-scanning the probe and the sample in X and Y directions to map and display the information on a monitor TV.

Among SPMs, AFM, in particular, is most widely used. AFM comprises a cantilever having a probe at its free end, an optical displacement sensor which detects the displacement of the cantilever, and a scanning mechanism which relatively scans the probe and the sample. As this optical displacement sensor, an optical lever type optical displacement sensor having high displacement detection sensitivity with a simple arrangement is most widely used.

In a commercially available atomic force microscope, the optical lever type optical displacement sensor applies a light beam having a diameter of 10 to 30 µm to the cantilever and detects a change in the reflection direction of the reflected light in accordance with the warpage of the lever through a two- or four-segments photodetector or the like, thereby outputting an electrical signal reflecting the movement of the probe at the free end of the cantilever.

The atomic force microscope maps the configuration of a sample surface by causing the scanning mechanism to control the Z-direction position of the probe with respect to the sample so as to keep the output of the optical displacement sensor constant while scanning the probe in the X and Y directions with respect to the sample, and displays the resultant information on the monitor of a computer.

The atomic force microscope has attracted attention as a device having the potential of allowing the observation of the manner of movement of a living biological sample in liquid with higher resolution than an optical microscope.

An optical microscope is a device which allows the observation of the manner of movement of a living sample. With the optical microscope, however, a sample cannot be observed with a resolution equal to or less than the wavelength of light due to the diffraction limit.

An electron microscope is a device which can realize high resolution on the nanometer order. The electron microscope, however, does not allow a measurement target to be placed in liquid, and hence does not allow the observation of a living biological sample in liquid.

In contrast to this, the atomic force microscope can be expected to realize high resolution on the nanometer order, and allows even the observation of a sample in liquid. Furthermore, the atomic force microscope can be easily combined with an optical microscope. This is one of the reasons why this device has attracted attention.

An optical microscopic observation method using a caged compound is also known. This observation method allows the observation of a specific reaction of a sample in real time by properly performing uncaging while optically observing the sample in the presence of the caged compound.

A caged compound is a generic term for molecules that are trapped in a "cage" and allowed to be released from the "cage" by an external stimulus. As a caged compound, a combination of a molecule A having physiological activation or fluorescent emission characteristics and a molecule B having photosensitivity is often used, in which the molecules A and B are bonded each other to restrain the physiological activation or fluorescent emission ability of the molecule A in advance, and the bond between the molecules A and B is allowed to be broken by an optical stimulus to release the molecule.

In the optical microscopic observation method using a caged compound, while a sample in liquid containing such a caged compound is optically observed, an optical stimulus is given to the caged compound by applying cage-photolytic light such as ultraviolet light to uncage the caged compound. This makes it possible to observe a reaction between the molecule released by cage release and the sample as an observation target such as a biological molecule. That is, this allows the time-series observation of the state of the sample before, during, and after the reaction between the sample and the molecule released by cage release.

When cage-photolytic light is to be applied, the position where a substance that can react with a sample, the amount of such substance, the timing when the substance is generated, and the like can be arbitrarily changed by controlling the range, strength, time, and the like of cage-photolytic light to be applied. After the cage-photolytic light is applied, the reaction of the sample is tracked by using a fluorescence label. In the optical microscope designed to perform this analysis, light for releasing a protecting group may be caused to come into focus with the target position of a sample being positioned in the visual field. Therefore, cage-photolytic light is applied to a target region upon confirmation of the application position of cage-photolytic light.

The atomic force microscope has the potential of being able to capture the morphological change of one biological molecule in liquid with a resolution on the nanometer order, if the scanning speed is sufficiently increased. In addition, mixing, in liquid, a molecule that reacts with a living molecule such as a protein or nucleic acid makes it possible to directly observe how the living molecule such as a protein or nucleic acid changes its structural form along with a biochemical reaction.

In order to observe the dynamic behavior of a living molecule, i.e., a sample, the sample must not be firmly fixed on a substrate and is partially fixed. Alternatively, the sample is bonded to a molecule fixed to the substrate to observe the dynamic behavior of the sample.

The sample, however, constantly undergoes Brownian motion, even if it is partially fixed to the substrate. That is, the sample is always in a dynamic state regardless of a reaction. It is therefore necessary to discriminate and recognize a change in dynamic state due to Brownian motion and a change in structural form due to a reaction. In practice, however, it is difficult to discriminate and recognize them. It is also difficult to prove that they are really discriminated.

The optical microscopic observation method using a caged compound can clarify the difference between the state before a reaction and the state after the reaction because the timing of releasing a caged compound can be controlled by the application of ultraviolet light. However, the optical microscope is insufficient in spatial resolution to image the structure or form of one molecule, and hence cannot image a change in the structure or form of one molecule.

Note that at the timing of cage release, the force acting between a sample and the probe at the cantilever sometimes changes due to the influence of the radiation pressure of photolytic light. In this case, the force exerted on the sample may reach the level at which the sample is destroyed.

Alternatively, around the cantilever, a solution may fluctuate in refractive index due to the migration caused by the spatial movement of a substance in the solution, e.g., a metal ion, polyion, or protein. As a result, noise that disturbs probe control may be superimposed on a cantilever displacement detection signal. In some case, the disturbance of probe control may reach the level at which the sample or probe is destroyed.

BRIEF SUMMARY OF THE INVENTION

The present invention is directed to a scanning probe microscope which allows real-time observation of a structural or morphological change in one molecule due to a biochemical reaction or a mechanical or electrical stimulus. A scanning probe microscope according to the present invention comprises a cantilever, a scanning mechanism which relatively scans the cantilever and a sample which exists in liquid, and an application mechanism which applies photolytic light to a caged compound existing in the liquid or the sample.

Another scanning probe microscope according to the present invention comprises a cantilever, a scanning mechanism which relatively scans the cantilever and a sample which exists in liquid, a detection mechanism which optically detects a displacement of the cantilever due to an interaction between the cantilever and the sample, an application mechanism which applies photolytic light to a caged compound existing in the liquid, an optical device which prevents photolytic light from reaching the detection mechanism, and an optical microscope which observes at least one of the sample, the cantilever, and a probe held on a free end of the cantilever.

Another scanning probe microscope according to the present invention comprises a mechanism which can switch a control signal to be applied to a Z piezoelectric element and a signal for holding a specific distance in order to control the distance between a sample and a probe on the basis of a displacement signal from a cantilever or the vibration state of the cantilever.

The present invention is directed to a molecular structure change observation method which allows real-time observation of a structural or morphological change in one molecule due to a biochemical reaction or a mechanical or electrical stimulus. The molecular structure change observation method according to the present invention includes a step of applying light which releases a protecting group of a caged compound existing in liquid or sample while scanning the sample in the liquid with a cantilever.

DETAILED DESCRIPTION OF THE INVENTION

An embodiment of the present invention will be described below with reference to the views of the accompanying drawing.

Figure 1:
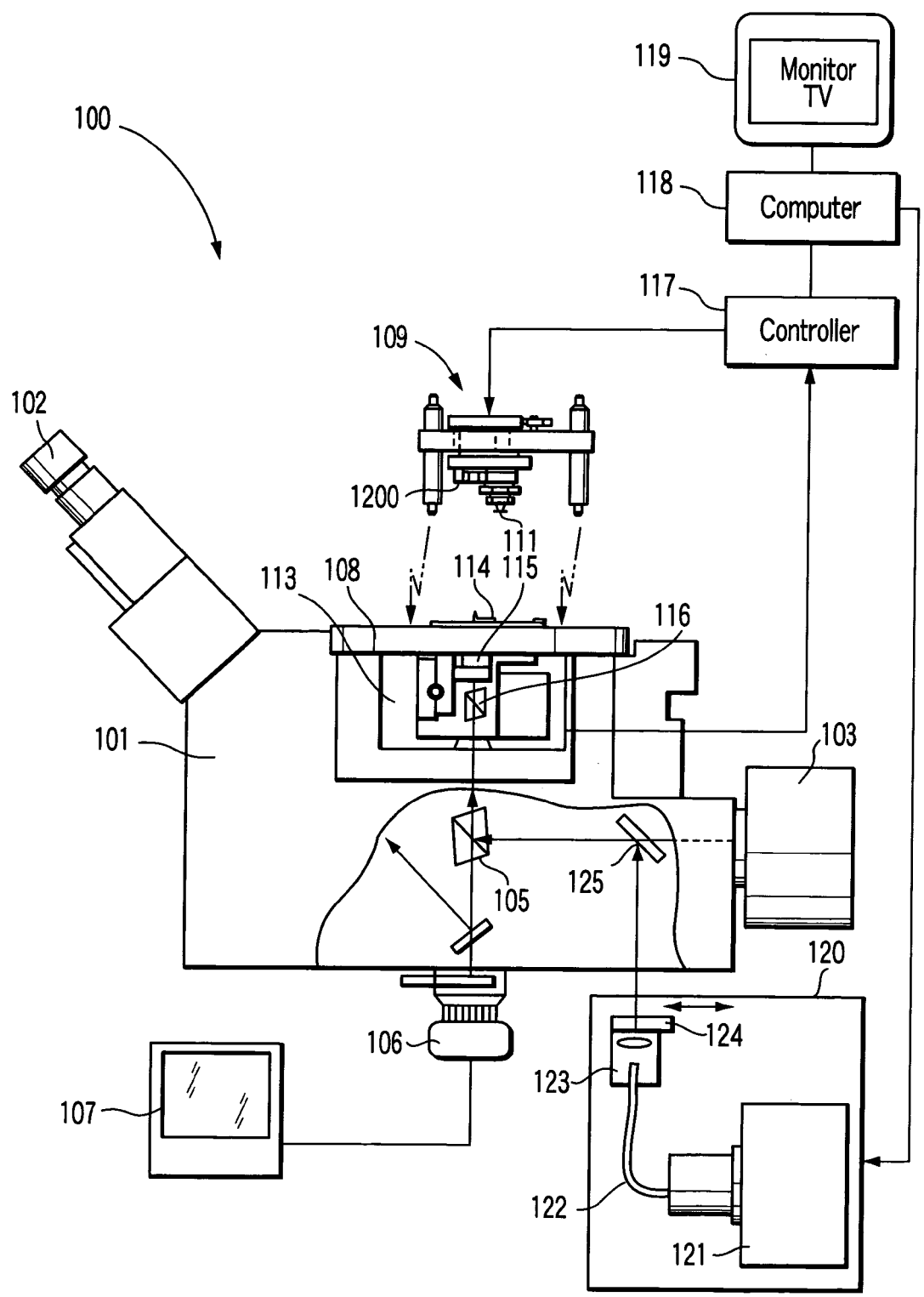
FIG. 1 is a view showing the overall arrangement of a scanning probe microscope according to the first embodiment of the present invention.

A scanning probe microscope according to an embodiment of the present invention will be described with reference to FIG. 1. FIG. 1 shows the overall arrangement of the scanning probe microscope according to this embodiment.

Referring to FIG. 1, a scanning probe microscope 100 basically comprises an atomic force microscope mechanism and a cage-photolytic light introduction mechanism using an inverted microscope.

The cage-photolytic light introduction mechanism, which is constituted by using a commercially available inverted microscope, includes a microscope housing 101, an eyepiece lens 102, an observation illumination light source 103, a dichroic mirror 105, a CCD camera 106, a TV monitor 107, and a cage-photolytic light source unit 120 which emits cage-photolytic light.

The cage-photolytic light source unit 120 includes a cage-photolytic light source 121 which emits cage-photolytic light, an optical fiber 122 which transfers cage-photolytic light, a lens unit 123 which properly restricts the spreading of a beam of cage-photolytic light, and a shutter 124 which controls the passage of cage-photolytic light.

The cage-photolytic light introduction mechanism further includes a mirror 125 for guiding the beam of cage-photolytic light emitted from the cage-photolytic light source unit 120 to the dichroic mirror 105.

When cage release is to be performed by using ultraviolet light, the cage-photolytic light source 121 comprises, for example, a mercury lamp, which is often used as an ultraviolet light source. Alternatively, the cage-photolytic light source 121 may comprise a light source which includes an yttrium YAG laser and is configured to emit 355-nm ultraviolet light by generating the third harmonic of light of the wavelength of the laser, which is 1,024 nm.

The shutter 124 opens and closes in accordance with a control signal supplied from a computer 118. The shutter 124 is controlled to intermittently open so as to make cage-photolytic light from the cage-photolytic light source unit 120 exit in a pulse form.

When the cage-photolytic light source 121 comprises a light source using an yttrium YAG laser, the cage-photolytic light source unit 120 can emit pulsed cage-photolytic light having a pulse width of several ns by controlling the yttrium YAG laser. Recently, laser light in the ultraviolet range is emitted from a semiconductor laser light source, which can be repeatedly turned on and off at high speed.

The atomic force microscope mechanism includes a plate-like structural member 108 which is fixed to the microscope housing 101, a cantilever 114 for detecting atomic force, a sample position adjusting mechanism 109 which includes a scanning mechanism 1200 for holding and scanning a sample, and an optical lever type optical sensor 113 for detecting the displacement of the cantilever.

The plate-like structural member 108 made of a low-thermal-expansion material (e.g., Invar) is mounted and fixed to the microscope housing 101 instead of a general stage. The sample position adjusting mechanism 109 and optical lever type optical sensor 113 are directly placed on the upper and lower sides of the plate-like structural member 108 fixed to the microscope housing of the inverted microscope.

The optical lever type optical sensor 113 is placed on the lower side of the plate-like structural member 108 and is supported by the plate-like structural member 108. The optical lever type optical sensor 113 includes an objective lens 115 and dichroic mirror 116. The objective lens 115 has both the function of an objective lens for inverted microscope observation and the function of the condenser lens of the optical lever type optical sensor 113. The dichroic mirror 116 separates sensor light of the optical lever type optical sensor 113 and light for cage release, and functions to prevent cage-photolytic light from entering the optical lever type optical sensor 113.

The sample position adjusting mechanism 109 includes the scanning mechanism 1200. A sample base glass 111 on which a sample is fixed is mounted on the scanning mechanism 1200. The sample position adjusting mechanism 109 is placed on the plate-like structural member 108 such that the sample base glass 111 mounted on the mechanism faces the cantilever 114.

The sample position adjusting mechanism 109 is stably placed on the plate-like structural member 108 by its own weight. This mechanism, however, may be fixed to the plate-like structural member 108 more firmly by using a rubber band made of Viton rubber or the like.

The atomic force microscope mechanism further includes a controller 117, the computer 118, and a monitor TV 119. The scanning mechanism 1200 and optical lever type optical sensor 113 are connected to the controller 117 and computer 118, and are controlled by them.

In the scanning probe microscope 100, the plate-like structural member 108, which is thick and high in rigidity, is placed at a position on the inverted microscope at which a stage is placed, and is fixed to the microscope housing 101. The plate-like structural member 108 is the main member of the atomic force microscope in terms of structure. The sample position adjusting mechanism 109 including the scanning mechanism 1200 and the optical lever type optical sensor 113 are placed on the upper and lower sides of the plate-like structural member 108. The scanning probe microscope 100 therefore has a structure which has rigidity high enough to realize scanning fast enough for the application to the observation of a biological sample, and is robust against vibration noise. This makes it possible to stably perform AFM observation.

In addition, the sample position adjusting mechanism 109 and optical lever type optical sensor 113 are placed directly above and below the plate-like structural member 108.

Figure 2:
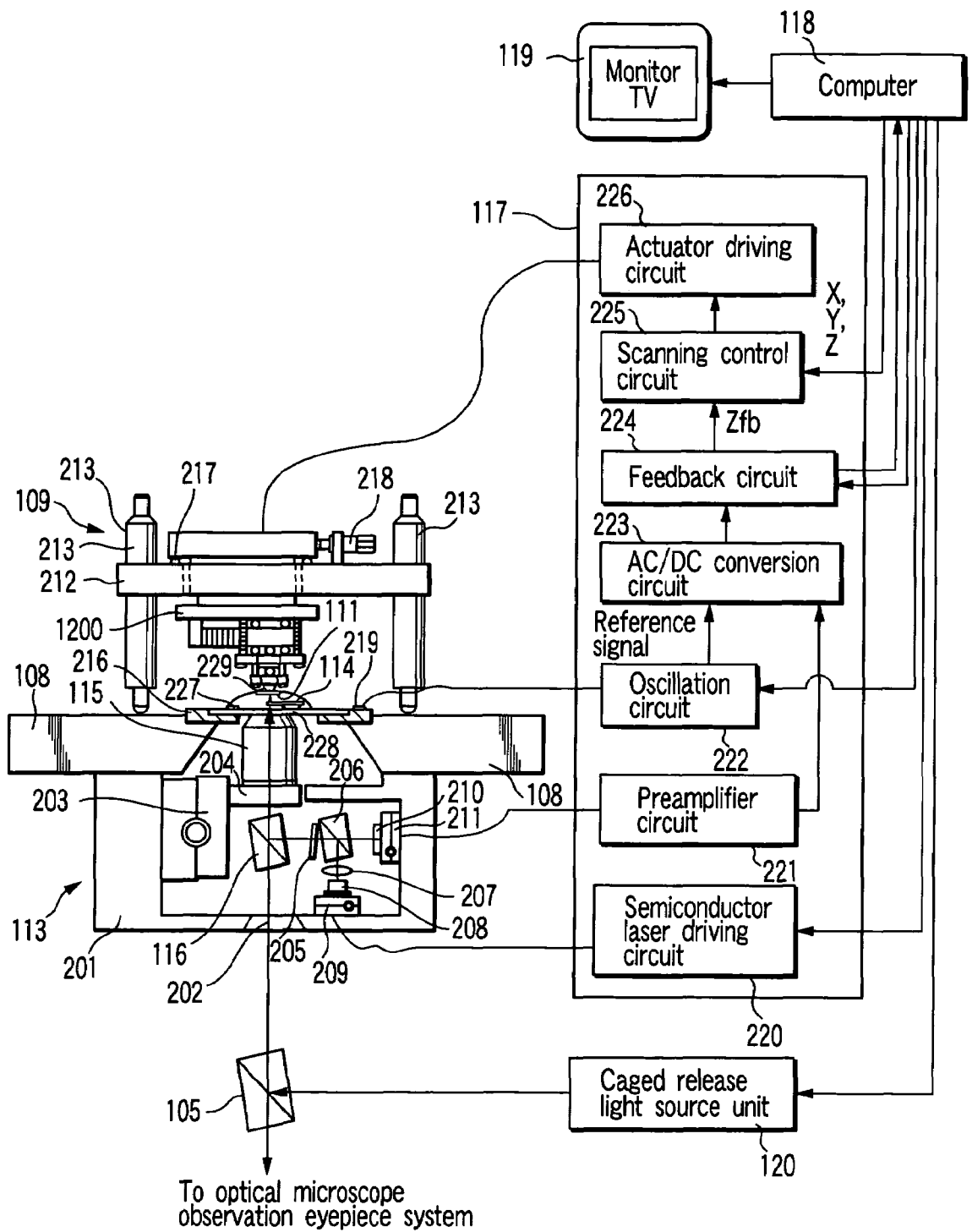
FIG. 2 is a view showing the arrangement of the main part of the scanning probe microscope in FIG. 1.

The atomic force microscope mechanism will be described in detail next with reference to FIG. 2. FIG. 2 shows the arrangement of the main part of the scanning probe microscope 100. The same reference numerals as in FIG. 1 denote the same members in FIG. 2.

The optical lever type optical sensor 113 includes a unit box 201 which accommodates the main optical elements of the sensor. The unit box 201 is fixed to the plate-like structural member 108 with screws.

The optical lever type optical sensor 113 includes, as the main optical elements accommodated in the position detection photodiode 210, the objective lens 115, an objective lens support base 204, a Z stage 203, the dichroic mirror 116, a ¼ wave plate 205, a polarizing beam splitter 206, a collimator lens 207, a semiconductor laser 208, a laser position adjusting stage 209, a position detection photodiode 210, and a photodiode position adjusting stage 211.

The dichroic mirror 116 is formed by bonding two triangular prisms, and has a rhombic shape. An end face of the dichroic mirror 116 is therefore tilted at an angle of approximately 3 to 4° with respect to the optical axis. This reduces the adverse effect of stray light caused by reflection by the end face of the dichroic mirror 116 on the optical lever type optical sensor 113.

The laser light emitted from the semiconductor laser 208 is converted into parallel light by the collimator lens 207. Of this light, only the light of a specific linearly polarized light component is reflected by the polarizing beam splitter 206. The reflected linearly polarized laser light is converted into circularly polarized light by the ¼ wave plate 205. This light is then reflected by the dichroic mirror 116 and is focused by the objective lens 115 to be applied to the back surface of the cantilever 114. The objective lens 115 has, for example, a magnification of 20×, and hence the spot diameter of laser light is reduced to approximately 2 μm. Even if a cantilever small in shape is used for high-speed AFM observation, the spot diameter of laser light is smaller than the width of the back surface of the cantilever. This makes most of sensor light from the optical lever type optical sensor be reflected by the cantilever back surface; little light reaches the sample placed above the cantilever 114.

The laser light reflected by the back surface of the cantilever 114 passes through the objective lens 115 and is reflected by the dichroic mirror 116. The resultant circularly polarized light is converted into linearly polarized light by the ¼ wave plate 205, propagates straight through the polarizing beam splitter 206, and is applied to the position detection photodiode 210. The displacement of the tip of the cantilever 114 due to the interaction with the sample moves the laser light spot on the position detection photodiode 210. The position detection photodiode 210 outputs an electrical signal reflecting this movement of the laser light spot to a preamplifier circuit 221.

The unit box 201 has an opening 202 in its lower side. The dichroic mirror 105 is placed below the opening 202. The dichroic mirror 105 guides cage-photolytic light from the cage-photolytic light source unit 120 to the objective lens 115 through the opening 202. The cage-photolytic light uncages a caged substance in liquid near a sample or the cantilever 114 or in the sample. The dichroic mirror 105 comprises a rhombic mirror prism like the dichroic mirror 116. This reduces the adverse effect of stray light caused by reflection by the end face of the mirror on an optical microscope observation image.

A transparent plate 228 is placed above the objective lens 115. The transparent plate 228 is held by the plate-like structural member 108 through a transparent plate holding member 216 which holds the peripheral portion of the transparent plate 228. The cantilever 114 is fixed to the transparent plate 228 with an adhesive. The cantilever 114 is placed facing upward so that the probe faces the sample base glass 111 and sample which are held facing downward.

The measurement modes of the atomic force microscope include an AC mode AFM measurement method which is executed while the cantilever is vibrated. The atomic force microscope mechanism further includes an excitation piezoelectric element 219 for vibrating the cantilever 114 to execute this AC mode AFM measurement method. The excitation piezoelectric element 219 is fixed to the transparent plate holding member 216 with an adhesive.

An AC voltage having a frequency near the resonance frequency of the cantilever 114 is applied from an oscillation circuit 222 to the excitation piezoelectric element 219. The excitation piezoelectric element 219 vibrates in accordance with the application of this AC voltage. This vibration is transferred to the transparent plate holding member 216 and transparent plate 228 to reach the cantilever 114. The cantilever 114 is resonated by the vibration of this frequency to greatly vibrate in the Z direction.

The sample position adjusting mechanism 109 includes the scanning mechanism 1200 and its support mechanism. The scanning mechanism 1200 is identical to that disclosed in Jpn. Pat. Appln. KOKAI Publication No. 2001-330425. The support mechanism includes a scanning mechanism support base 212 which supports the scanning mechanism 1200, three micrometer heads 213 (only two of them are shown in FIG. 2) which three-point support the above components on the plate-like structural member 108, and a coarse adjustment mechanism 218 provided for the scanning mechanism support base 212. The coarse adjustment mechanism 218 is a mechanism using a micrometer and can move the scanning mechanism 1200 with respect to the scanning mechanism support base 212.

The scanning mechanism 1200 is three-point supported on the scanning mechanism support base 212 by three abutment members 217 (only two of them are shown in FIG. 2), and is not moved by light force or vibration owing to its own weight. By moving the scanning mechanism 1200 with respect to the scanning mechanism support base 212 using the coarse adjustment mechanism 218, the sample is moved in the X and Y directions. In addition, the sample is moved in the Z direction by changing the height position of the scanning mechanism support base 212 by adjusting the three micrometer heads 213.

The scanning mechanism 1200 includes a Z scanning actuator which is in charge of Z-direction scanning, an X scanning actuator which is in charge of X-direction scanning, and a Y scanning actuator which is in charge of Y-direction scanning. The scanning mechanism 1200 further includes a sample holding member 229 in the form of a truncated cone, which is fixed to the lower end of the Z scanning actuator. The sample base glass 111 holding the sample is fixed to the lower end of the sample holding member 229 through silicone grease. This fixing is performed by applying silicone grease to the sample holding member 229 and sample base glass 111 and lightly pressing them to each other.

Referring to FIG. 2, the sample, sample base glass 111, cantilever 114, and the like are held in liquid 227. The liquid 227 covers portions near the sample and cantilever 114 owing to the surface tension.

The atomic force microscope mechanism allows observation in liquid, which is an essential requirement for the observation of a living biological sample. Even if, therefore, a sample is placed in liquid, the scanning probe microscope 100 allows optical microscope observation and atomic force microscope observation.

The atomic force microscope mechanism is combined with the controller 117, computer 118, and monitor TV 119. These components control and drive the atomic force microscope mechanism, perform signal processing, and finally display configuration information on the sample on the monitor TV, thereby allowing the user to obtain findings concerning the surface information of the sample.

The controller 117 includes, for example, a semiconductor laser driving circuit 220, the preamplifier circuit 221, the oscillation circuit 222, an AC/DC conversion circuit 223, a feedback circuit 224, a scanning control circuit 225, and an actuator driving circuit 226.

In the scanning probe microscope 100, before the observation of a biological molecule, a portion around the cantilever is observed to adjust the application position of sensor light from the optical lever type optical sensor 113 with respect to the cantilever 114. In this case, although not shown, the mirror 125 is removed from the optical path to introduce light from the observation illumination light source 103 to the objective lens 115, and the dichroic mirror 105 is replaced with a mirror prism which transmits the wavelength of the sensor light.

Figure 3:
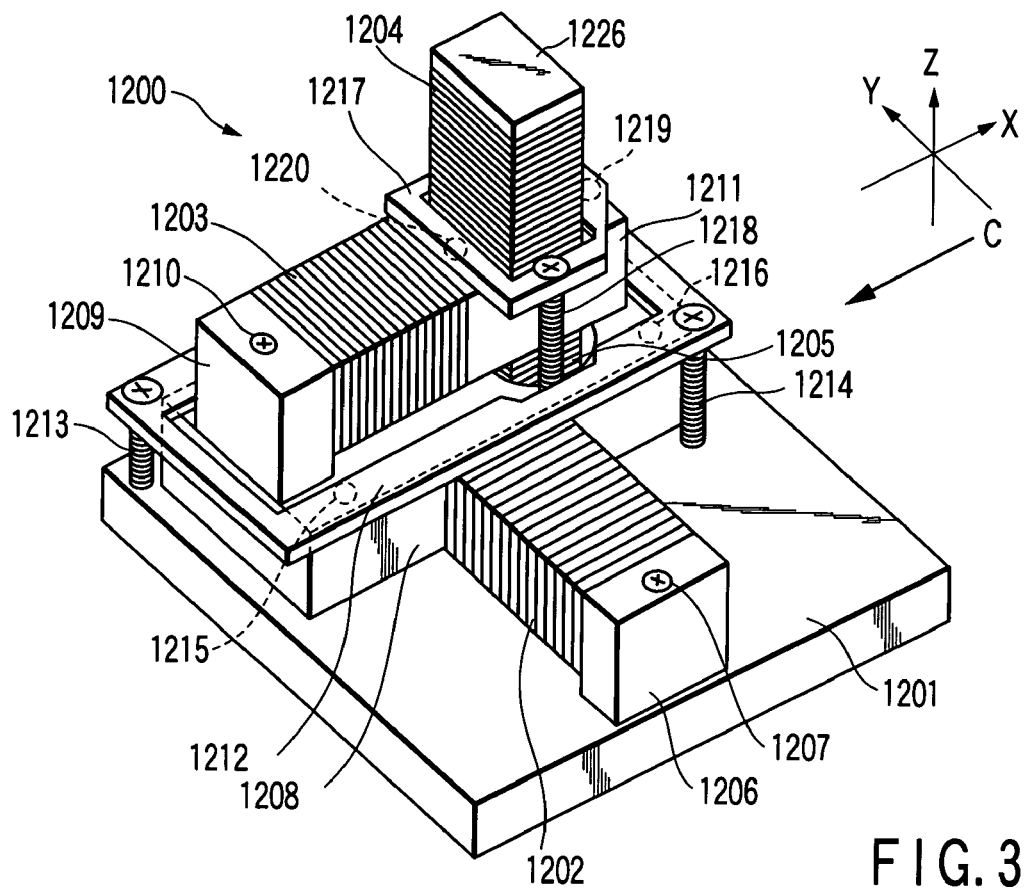
FIG. 3 is a perspective view of a scanning mechanism shown in FIGS. 1 and 2.
Figure 4:
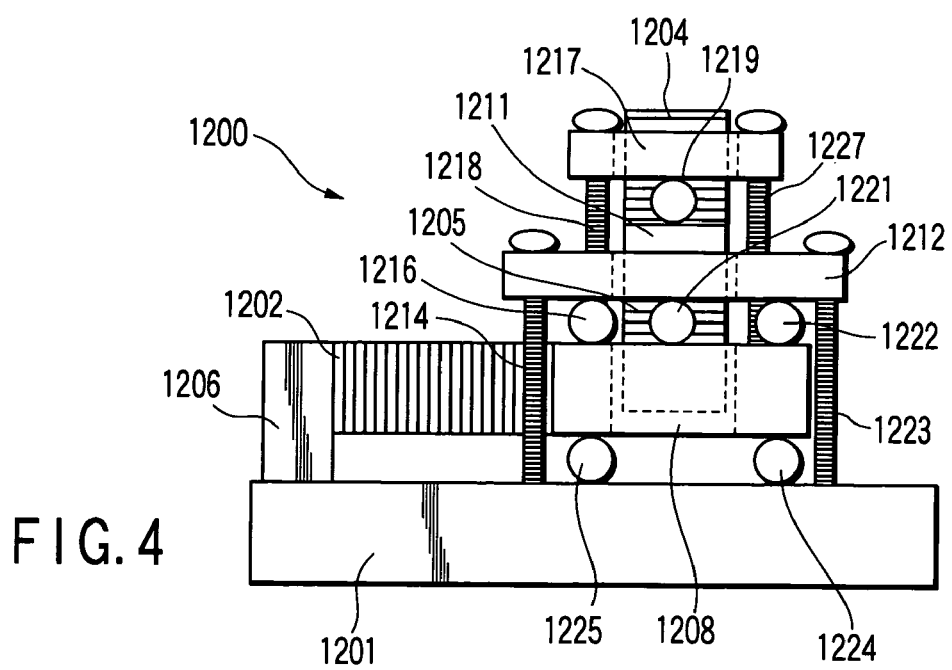
FIG. 4 is a side view of the scanning mechanism in FIG. 3 when viewed from the direction indicated by an arrow C.

The scanning mechanism 1200 will be described next with reference to FIGS. 3 and 4. FIG. 3 is a perspective view of the scanning mechanism. FIG. 4 is a side view of the scanning mechanism in FIG. 3 when viewed from the direction indicated by an arrow C. Note that in scanning operation, the cantilever may be driven to be scanned relative to the sample.

The scanning mechanism 1200 includes a scanning mechanism holding base 1201 which is a base plate, a first actuator holding portion 1206 which is fixed to the base, a Y scanning actuator 1202 which is mounted on the first actuator holding portion 1206 and can stretch and contract along the Y-axis, a block 1208 mounted on the other end of the Y scanning actuator 1202, a second actuator holding portion 1209 which is fixed to the block 1208, an X scanning actuator 1203 which is mounted on the second actuator holding portion 1209 and can stretch and contract along the X-axis, an actuator coupling portion 1211 which is mounted on the other end of the X scanning actuator 1203, and two actuators 1204 and 1205 which are fixed to the actuator coupling portion 1211 and can stretch and contract along the Z-axis.

The two actuators 1204 and 1205 and the actuator coupling portion 1211 constitute a Z scanning actuator. The sample holding member 229 is mounted on a free-end side 1226 of the actuator 1204 as a component of the Z scanning actuator. The first actuator holding portion 1206 is fixed to the scanning mechanism holding base 1201 with a screw 1207. The second actuator holding portion 1209 is fixed to the block 1208 with a screw 1210.

As shown in FIG. 4, the block 1208 which is moved along the Y-axis in accordance with the driving operation of the Y scanning actuator 1202 is positioned between the scanning mechanism holding base 1201 and a pressure plate 1212, and is sandwiched between minute balls 1216, 1222, 1224, 1225, and 1215 (see FIG. 3). The spacing between the scanning mechanism holding base 1201 and the pressure plate 1212 is adjusted by screws 1213 and 1214 so as to be fixed parallel to each other. This imposes a restriction on the movement of the block 1208 along the Z-axis without imposing a large restriction of the movement along the Y-axis.

The actuator coupling portion 1211 which is moved along the X-axis in accordance with the driving of the X scanning actuator 1203 is positioned between the block 1208 and a second pressure plate 1217. The actuator coupling portion 1211 is supported from above by minute balls 1219 and 1220, and supported from below by a minute ball 1221. This imposes a restriction on the movement of the actuator coupling portion 1211 along the Z-axis. The spacing between the block 1208 and second pressure plate 1217 is adjusted by screws 1218 and 1227 so as to be fixed parallel to each other. This imposes a restriction on the movement of the actuator coupling portion 1211 along the Z-axis without imposing a large restriction on the movement along the X-axis.

In this manner, in the scanning mechanism 1200, the flexure and vibration of the Y scanning actuator 1202 are restricted by a rolling or sliding guide including the pressure plate 1212, the screws 1213 and 1214, and the minute balls 1216, 1215, 1222, 1224, and 1225. In addition, the flexure and vibration of the X scanning actuator 1203 are restricted by a rolling or sliding guide including the pressure plate 1217, the screws 1218 and 1227, and the minute balls 1219 and 1220.

The scanning mechanism 1200 therefore has mechanical rigidity high enough to realize high-speed scanning sufficient for application to the observation of a biological sample, and generates little vibration.

Figure 5:
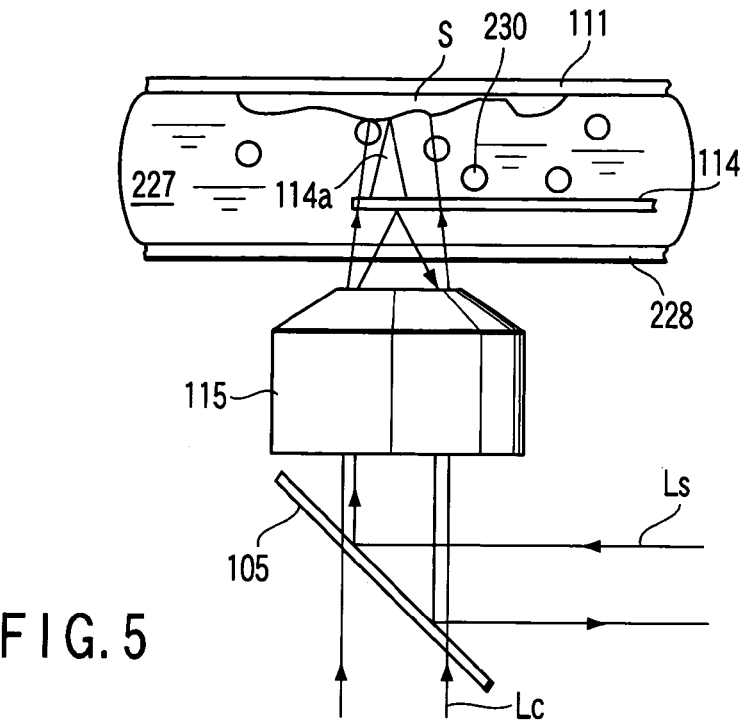
FIG. 5 is a view schematically showing a portion around a cantilever at the time of observation of a molecular structure change with the scanning probe microscope in FIG. 1.

The operation of the scanning probe microscope 100 according to this embodiment, i.e., a molecular structure change observation method according to this embodiment, will be described below with reference to FIG. 5. FIG. 5 schematically shows a portion around the cantilever. The same reference numerals as in FIG. 2 denote the same members in FIG. 5.

As shown in FIG. 5, the liquid 227 held on the transparent plate 228 surrounds the sample base glass 111 and cantilever 114. This liquid contains a caged compound 230. The caged compound 230 is, for example, a substance obtained by bonding a photosensitive molecule to a low-molecular compound (e.g., ATP, $Ca^{2+}$, or Glu) which reacts with a sample S, which is a biological molecule, so as to prevent the expression (to be referred to as caging hereinafter) of a biochemical/physiological function. The caged compound 230 obtained in this manner is uncaged in response to an optical stimulus within a short period of time, thereby instantly generating a compound having activity.

The scanning probe microscope 100 scans the sample S in the X and Y directions with respect to a probe 114a positioned at the free end portion of the cantilever 114 by causing the scanning mechanism 1200 to move the sample S held on the sample base glass 111. During this XY scanning, the optical lever type optical sensor 113 applies sensor light Ls to the free end portion of the cantilever 114 and monitors the displacement of the free end portion of the cantilever 114, i.e., the probe 114a. The controller 117 controls the Z-direction position of the sample S with respect to the probe 114a by causing the scanning mechanism 1200 to move the sample S held on the sample base glass 111 so as to keep a detection signal from the optical lever type optical sensor 113 constant, or in operation in the AC mode, an output signal from the AC/DC conversion circuit 223 constant, which corresponds to the amplitude value of the detection signal from the optical lever type optical sensor 113. The computer 118 acquires information on the surface shape of the sample S (to be referred to as mapping hereinafter) on the basis of a series of these control signals, XY scanning signals, and Z control signals, and displays the resultant image on the monitor TV 119. In addition, the computer 118 records it as needed.

The scanning probe microscope 100 applies the cage-photolytic light Lc to a region near the probe 114a by the cage-photolytic light source unit 120 while acquiring the shape of the surface of the sample S in this manner. Upon reception of the cage-photolytic light Lc, the caged compound 230 releases the caged and instantaneously generates a compound having activity. The compound having activity generated in this manner reacts with the biological molecule S which is the sample.

The scanning probe microscope 100 keeps mapping the surface shape of the sample S which is, for example, a biological molecule, even during the progress of the chemical reaction between the compound having activity generated by cage release and the biological molecule S which is the sample. Therefore, the progress of the reaction between the compound having activity and the biological molecule S is observed in real time. In this manner, images in the states before, during, and after this reaction can be acquired.

The scanning probe microscope 100 controls the timing of generation of a compound having activity which can react with a biological molecule as an observation target by the application of cage-photolytic light. This makes it possible to substantially control the timing of a reaction between a compound having activity and a biological molecule. As a consequence, the images of the biological molecule before and after the reaction can be obtained. This makes it possible to clearly discriminate and recognize a change in the dynamic state of a biological molecule due to Brownian motion and a change in the structural form of the biological molecule. That is, a change in molecular structural form due to the reaction of a biological molecule can be observed.

A concrete example in which the scanning probe microscope 100 of this embodiment is applied to the observation of a change in the molecular structure of myosin V, which is one of the transport proteins in the brain, using caged ATP and caged $Ca^{2+}$ will be described next.

The myosin family is motor proteins, and converts the energy generated by ATP hydrolysis into mechanical energy. Studies have been made for a long time without success to explain the mechanism for this conversion. There has been an old hypothesis that a large structural change that might occur during an ATP decomposition reaction cycle of myosin dynamically acts. However, since such a phenomenon has not been able to be viewed directly, no clear evidence has been obtained.

Figure 7:
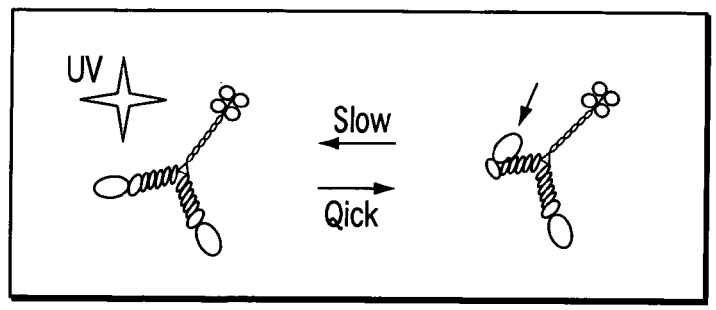
FIG. 7 is a view schematically showing a structural form change in myosin V in the reaction in FIG. 6.
Figure 6:
FIG. 6 is a view showing a change in the structural form of myosin V before and after the generation of ATP from caged ATP, i.e., images of myosin V before the application of cage-photolytic light (I), immediately after the application (II), and some time after the application (III)

In a concrete example, caged ATP was mixed in a system obtained by causing mica to partially adsorb myosin in a buffer solution, and images of the biological molecule S before and after the application of cage-photolytic light to the system were consecutively acquired by using the high-speed scanning probe microscope 100. FIG. 6 shows images of the biological molecule S obtained in this manner before the application of cage-photolytic light (I), immediately after the application of the cage-photolytic light (II), and some time (several sec) after the application of the cage-photolytic light (III). FIG. 7 schematically shows a change in the structural form of the biological molecule S due to the reaction upon the application of the cage-photolytic light.

Myosin V has four calmodulin molecules bonded to its neck region in the absence of calcium. When calcium is added to the myosin, the calcium is bonded to calmodulin, and the calmodulin is dissociated from the neck region.

Figure 9:
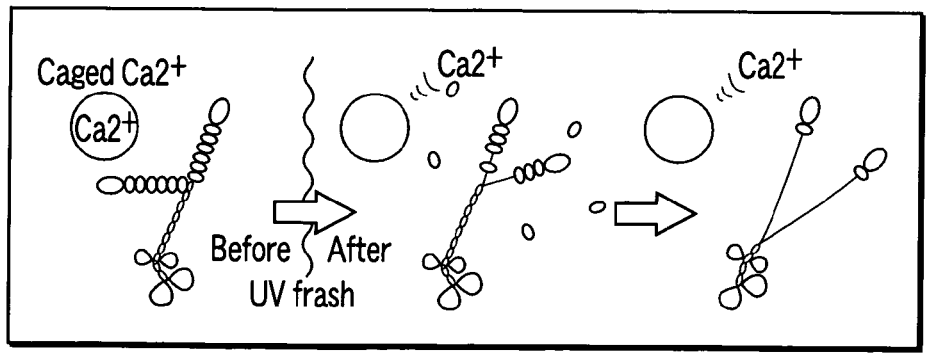
FIG. 9 is a view schematically showing a change in the structural form of myosin V due to the reaction in FIG. 8.
Figure 8:
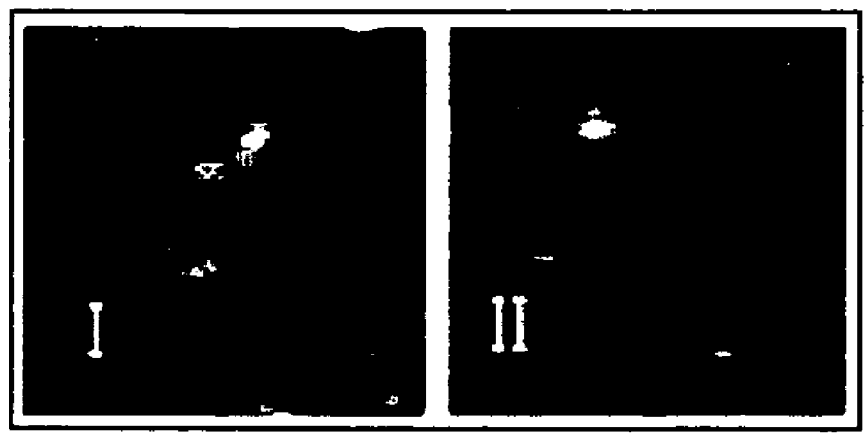
FIG. 8 is a view showing a change in the structural form of myosin V before and after the generation of $Ca^{2+}$ from caged $Ca^{2+}$, i.e., images of myosin V before the application of cage-photolytic light (I) and after the application (II)

In another concrete example, the high-speed scanning probe microscope 100 was used to consecutively obtain images of the biological molecule S before and after the application of photolytic light by using caged $Ca^{2+}$. FIG. 8 shows the images of the biological molecule S obtained in this manner before the application of the cage-photolytic light (I) and after the application of the cage-photolytic light (II). FIG. 9 schematically shows a change in the structural form of the biological molecule S due to a reaction upon the application of the cage-photolytic light.

As is obvious from these concrete examples, the scanning probe microscope 100 or molecular structure change observation method according to this embodiment is excellent in that a biochemical reaction and the structural form of a biological molecule can be observed synchronously, and the cause for a change in the structural form can be directly attributed to the reaction.

The scanning probe microscope and molecular structure change observation method according to the present invention are therefore expected to become popular and widely used. For example, the present invention can be used for biological studies and experiments, verification, and the like for pharmaceutical development and medical treatment.

The above reaction is influenced by the environment or the presence of a catalyst, e.g., the presence of pH or an ion. If sequence control is performed for the conditions for causing a reaction, phenomena before and after the conditions are satisfied can be grasped and compared. The timing and duration of a change from the state of caged compound to an activated state are controlled by letting a substance or molecule required for a reaction exist in liquid in the state of a caged compound and controlling the application time of cage-photolytic light. The caged compound is present near the sample as well in the liquid. When, therefore, the compound is uncaged, a reaction occurs at the moment or within a short period of time. This makes it easy to grasp the difference before and after the reaction. This time is influenced by the concentration of the caged compound and other conditions. Since a reaction can be started instantly, the result on only a target reaction can be sequentially observed and measured immediately after the reaction. This makes it possible to track a target molecule or bonded molecule.

In the above embodiment, cage-photolytic light for uncaging a caged compound is applied from below through the objective lens which is shared with the optical lever type optical sensor for detecting the displacement of the cantilever. However, the application form of cage-photolytic light is not limited to this. Cage-photolytic light may be applied from side or applied from above through the sample base glass 111.

A caged compound may be introduced into a tissue or cell by injection. For a study theme on cell membranes or membrane proteins, a caged compound may be introduced into a capillary by using a patch clamp method. A protein, substance, or ion which contributes to nuclear membrane elimination is caged to be functionalized at the tip of probe, and is made to contact a nuclear membrane or is introduced near to it. Cage-photolytic light is then applied to the caged compound. This makes it possible to conduct an experiment to clarify the mechanism for nuclear membrane elimination at the time of cell division. In contrast to this, an RNA binding protein for adsorbing RNA (ribonucleic acid) is caged to be functionalized at the tip of the probe, and cage-photolytic light is applied upon insertion of the probe into the nucleus. This makes it possible to control the extraction amount of RNA in the nucleus.

Force curves may be measured on a target molecule or in a predetermined place before and after cage release.

The cantilever or probe may be functionalized with a molecule or functional group, and a two-dimensional sensor such as a four-segments diode may be used to detect the displacement of the free end of the cantilever so as to detect a reaction with the molecule while scanning the reaction. An experiment is conducted in which the cantilever or probe is functionalized with a caged protein molecule and the bond between the functionalizing protein molecule and another protein or substance which is specifically bonded thereto is detected. When this bonding force or a predetermined boding force is detected, photolytic light is applied. Since bonding force is continuously measured, the elimination of bonding force or a change in bonding force, i.e., an increase in boding force, can be known.

As cage-photolytic light, light in the visible or infrared range may be used other than ultraviolet light. Although light in the visible or infrared range is lower in energy than ultraviolet light, sufficient energy for cage release can be obtained by using the two-photon effect or multi-photon effect. With these wavelength bands, since the toxicity against a living organism such as a protein is low, an observation result with fewer artifacts can be obtained as compared with the case wherein ultraviolet light is directly applied.

Figure 10:
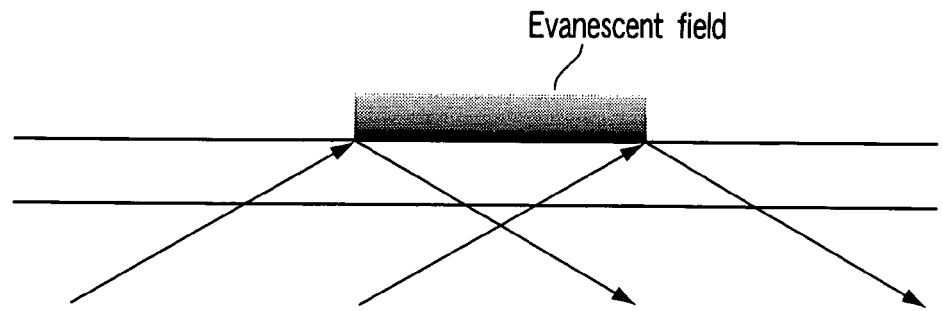
FIG. 10 is a view schematically showing the generation of an evanescent field by total reflection.

Although this embodiment has exemplified the inverted microscope, the present invention need not be limited to this, and an erecting microscope may be used. The layout of the cantilever, illumination or excitation optical system, and observation optical system can be selected within a feasible range. For example, referring to FIG. 5, observation may be made from above the sample base glass 111. As an illumination or excitation optical system, a transmission type or epi-illumination type may be used. Illumination light or excitation light may be introduced from the side with the probe of the cantilever or the side without the probe. In addition, as shown in FIG. 10, as a method of supplying energy for cage-photolytic light, a method using an evanescent field is available. Light or laser light is totally reflected by the opposite side of the substrate to the side on which a sample is placed or fixed. At this time, an evanescent field is generated near the surface of the substrate on which the sample is mounted. An experiment is conducted in which a fluorescent substance is made to emit fluorescence. By using ultraviolet light or laser light as light to be totally reflected, cage release can be performed only in a place near the surface of the substrate on which the sample exists. These optical microscopes can be configured as devices which apply excitation light and perform observation as well as applying photolytic light.

Furthermore, an optical microscope can be configured as a scanning confocal microscope. Scanning methods for the confocal microscope include, for example, a method of two-dimensionally or three-dimensionally scanning light brought into focus at a position conjugate to a pinhole, a method of rotating a disk in which a pinhole or slit is formed, and a method of using two-photon or multi-photon excitation of making photons act on a fluorescent substance. The effect of a confocal optical system using a confocal microscope is that a region in which fluorescence is excited can be limited and designated spatially as well as temporally. That is, a region in which fluorescence is excited is part of the surface of a cell or an organelle or nucleus in a cell. The spatial spread of this region is adjusted from one micron or less up to an application region with a non-confocal system in accordance with purposes. According to the experiment disclosed in "Molecular Biology Third Edition", Kyoikusha, a spindle shape is formed in a cell stage, and light can be applied to only a plane crossing one of microtubules holding a chromosome string in a central portion of the spindle shape. Cage release can be done by using ultraviolet light as this light. In addition, the manner of decomposition and growth of a microtubule can be observed by using a fluorescent substance which labels the microtubule. At this time, the cantilever is used to detect the force with which a chromosome moves on a microtubule or the force with which a protein molecule which transports a chromosome moves. Note that the scanning confocal microscope may use the objective lens 115 as its objective lens and be arranged at a lower position in FIG. 5, or may be arranged at an upper position in FIG. 5 by using another objective lens.

The effect obtained by limiting the light application space of the confocal optical system is that the probability of influence on the laser optical system for the detection of the displacement of the free end of the cantilever can be reduced. Light passing through the pinhole on the illumination light/excitation light side forms a light beam in a space near the sample, which is more limited than that of the optical system of the imaging system. Assume that this light beam is prevented from striking the cantilever, being scattered and guided to the detector for the detection of a displacement, and influencing the detection. In this case, a region as close to the cantilever as possible can be scanned within the spread of the sample in the range. If conditions allow, a region subjected to scattering by the cantilever and a region not subjected to scattering may be repeatedly scanned during scanning of the confocal optical system. In this case, using a confocal optical system will relatively increase the range subjected to scattering as compared with the case of the optical system of the imaging system. Like an optical microscope, a scanning confocal microscope can be configured as a device which applies excitation light and performs observation as well as applying photolytic light.

The application of photolytic light/excitation light/illumination light by the optical microscope including the scanning confocal microscope may influence the detection of the displacement of the free end of the cantilever as long as the duration of influence is short enough to be allowed in terms of the observation data obtained by the scanning probe microscope. On the other hand, spatial and temporal limitations can be eliminated by discriminating light to be used among photolytic light, excitation light, illumination light, observation light, light for the detection of the displacement of the free end of the cantilever, and the like according to the wavelengths by using the grating method or the method disclosed in Jpn. Pat. Appln. KOKAI Publication No. 8-404420.

As methods of reducing the probability of influence on the laser optical system for the detection of a displacement, there have been presented the method of shortening the application time, for example, in a case wherein a general microscope is used, and the method based on the effect obtained by limiting a light application space, for example, in a case wherein a confocal microscope is used. In each system, however, it is sometimes necessary to apply photolytic light for a period of time long enough to influence the laser optical system of the displacement detection system, apply light to a wide region, or apply high energy. In this case, the following influence may appear in the cantilever displacement detection system and feedback control system. An offset unrelated to the actual displacement of the cantilever acts on the displacement detector or the probe is pressed against a sample at a speed exceeding the feedback speed due to the radiation pressure of light applied. This may be a cause for damage to the sample or probe.

In order to prevent this, the following methods are effective: a method of temporarily stopping sample/probe control while holding a signal applied to the Z piezoelectric element at the control voltage which has been applied immediately before the application of photolytic light in accordance with the timing of the application of photolytic light; and a method of retracting the probe or sample by a predetermined distance by applying a voltage for increasing the distance between the sample and the probe in addition to the control voltage which has been applied immediately before the application of photolytic light. As a method for retraction, a method of increasing the distance up to a specific retraction height with respect to the Z piezoelectric element may be used. There is also an effective method in which the coarse adjustment mechanism is used to set a state wherein the probe does not reach a sample within the control range for the Z piezoelectric element, without changing control operation, and photolytic light is applied thereafter.

The cantilever 114 in FIG. 5 may be replaced with the cantilever and device for a near field optical microscope which are disclosed in Japanese Patent No. 3268797. This makes a scanning near field optical microscope as one of scanning probe microscopes become a device having a cage release function. Introduction of a caged compound and temporal and spatial control and limitations on cage release are the same as those in the case wherein the cantilever 114 is used.

The following is an example in which a reactant, e.g., a metal ion, polyion, or protein, is spatially localized in one place, and a signal for release, e.g., a voltage, current, light, or flow, is input, thereby causing a change in a sample, e.g., a cell or molecule, which is to be observed by an atomic force microscope.

Figure 11:
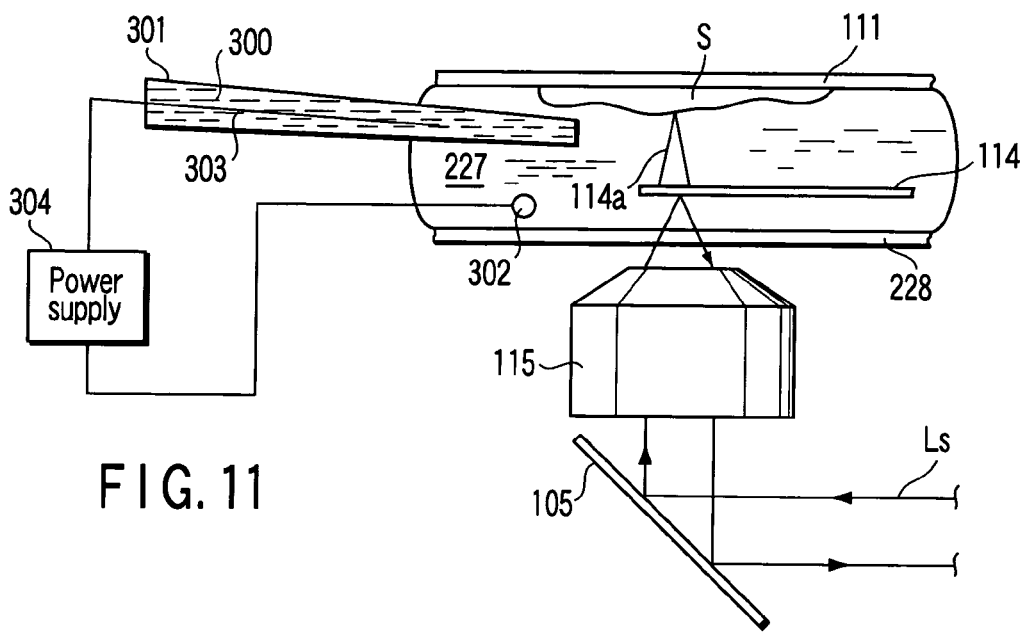
FIG. 11 is a view showing an arrangement for supplying a substance which reacts with a sample S into a solution around the sample.

FIG. 11 shows an arrangement for supplying a substance which reacts with the sample S into liquid around the sample.

As shown in FIG. 11, first of all, a substance 300 which causes a change in a sample at a specific concentration is concealed in a small tube (capillary) 301 having a hole in its distal end through which the substance 300 can barely pass.

The distal end portion of the capillary 301 and a counter electrode 302 are placed in liquid containing the sample S and cantilever 114.

An electrode 303 is inserted in the capillary 301, and one of the electrodes of a power supply 304 is connected to the electrode 303. The other electrode of a power supply 304 is connected to the counter electrode 302. The power supply 304 controls the potential difference between the counter electrode 302 and the electrode 303 in the capillary. When a potential difference is applied to the inside and outside of the capillary, an ionic substance existing in the capillary moves as an ion current from the small hole of the distal end of the capillary to liquid region 227 in which the sample exists.

The substance 300 which causes a change in the sample S may be a substance with ionicity or a neutral substance which moves in accordance with the flow of the ionic substance.

Capturing and comparing images before and after the action of the power supply 304 make it possible to observe the influences of the substance 300 on the sample S.

The power supply 304 may be connected to a controller which controls measurement and image capturing by the atomic force microscope, which is not described, to generate a potential difference in accordance with a specific timing of image capturing. In addition, as the power supply 304, a power supply having a current control function may be used.

A structure which partitions a space in the distal end of the capillary 301 is not limited to a small hole. It suffices to use any structure which limits the transmission of the reactant 300 and ions as ion current sources due to Brownian motion considerably as compared with movement due to an ion current. For example, a porous polymer film, ceramic, gel substance, ion channel, or the like may be used.

Referring to FIG. 11, the distal end of the capillary 301 is placed in the solution 227. If, however, the sample S is a cell, the distal end may be inserted into the cell. In this case, the position where the reactant 300 is to be supplied can be limited to the inside of the cell.

Figure 12:
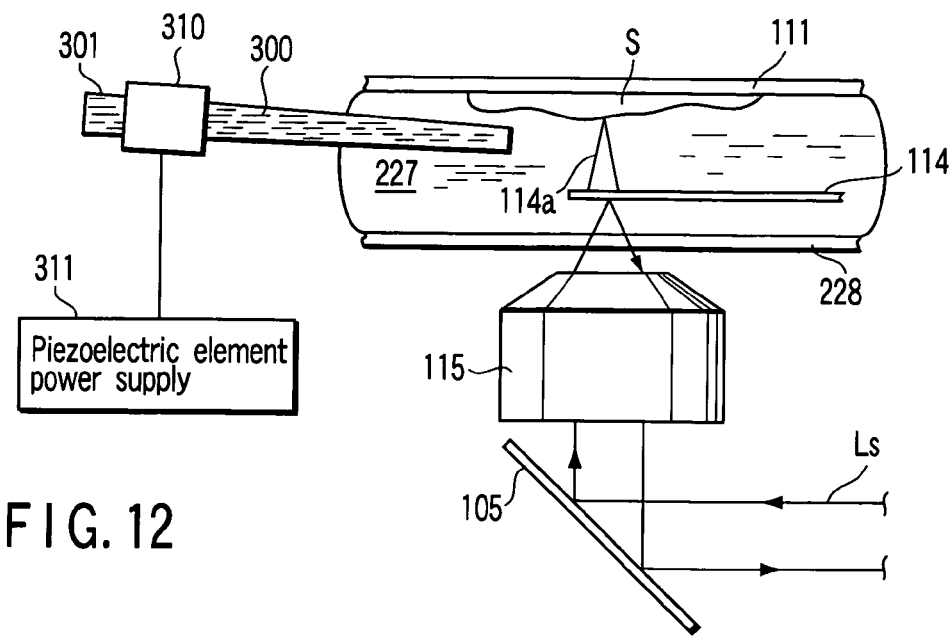
FIG. 12 is a view showing another arrangement for supplying a substance which reacts with the sample S into the solution around the sample.

FIG. 12 shows another structure for supplying a substance which reacts with the sample S into liquid around the sample.

As shown in FIG. 12, a tubular piezoelectric element 310 is provided around the capillary 301 to add a function of changing the volume of the capillary 301. The piezoelectric element 310 vibrates in accordance with the supply of a signal from a piezoelectric element power supply 311 to change the volume of the capillary 301. This makes the reactant 300 be forcibly discharged from the distal end of the capillary 301.

In the arrangement shown in FIG. 12, if vibrations accompanying fluctuations in volume have influences, the distal end portion of the capillary 301 and the portion in which fluctuations in volume occur may be connected through a tube made of a flexible material so as to prevent vibrations from being transferred to the distal end portion of the capillary 301.

Referring to FIG. 12, a heater may be provided in place of the tubular piezoelectric element 310. In this case, by heating the capillary 301 using the heater, a solution (reactant 300) in the capillary 301 is evaporated or the capillary 301 itself is expanded and contracted so as to change the volume in the capillary, thereby forcibly discharging the reactant 300 from the distal end of the capillary 301.

Figure 13:
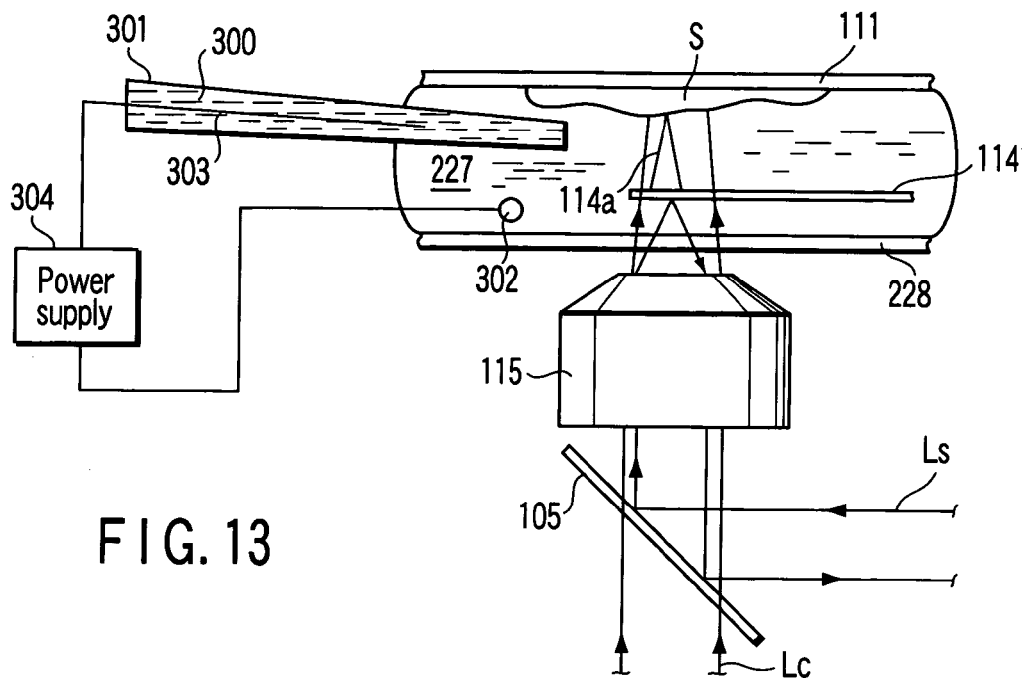
FIG. 13 is a view showing an arrangement obtained by combining a mechanism which applies cage-photolytic light with the arrangement in FIG. 11.

A mechanism for applying the cage-photolytic light Lc may be combined with the arrangements shown in FIGS. 11 and 12. FIG. 13 shows, as an example of such an arrangement, an arrangement obtained by combining a mechanism for applying the cage-photolytic light Lc with the arrangement shown in FIG. 11.

Referring to FIG. 13, the cage-photolytic light Lc is transmitted through the dichroic mirror 105 and applied into liquid near the cantilever 114 through the objective lens 115.

In this arrangement, the reactant 300 is used as a caged reagent, and the timing of introduction of the caged reagent is synchronized with the timing of application of the cage-photolytic light Lc, thereby allowing observation of the reaction of the sample S even with a small amount of caged reagent.

The mechanism for avoiding the influence of cage-photolytic light on the displacement of the cantilever has been described above. Assume that a reactant, e.g., a metal ion, polyion, or protein, is spatially localized in one place, and a signal for release, e.g., a voltage, current, light, or flow, is input, thereby causing a change in a sample, e.g., a cell or molecule, which is to be observed by an atomic force microscope. Even in this case, when the spatially localized state is changed, a flow is produced in the liquid to result in an abrupt displacement of the cantilever itself or a nonuniform refractive index state. This may cause disturbance to the displacement detection system for the cantilever.

In order to prevent a disturbance during the application of the above photolytic light while such a disturbance is occurring, a method of holding a distance between the sample and the probe or retracting the sample or probe is effective.

Figure 14:
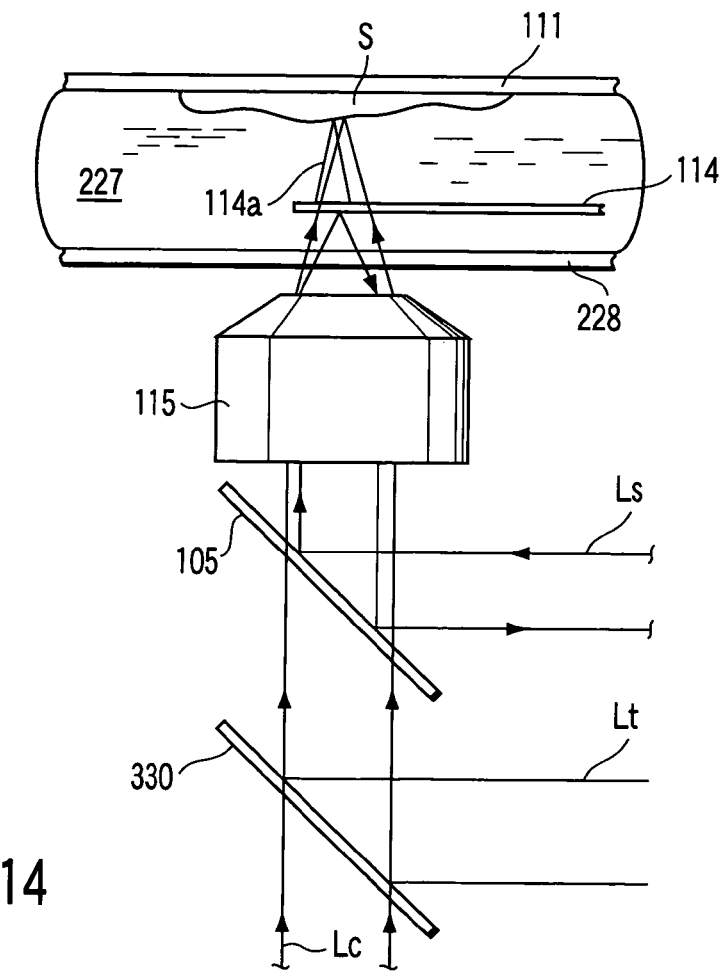
FIG. 14 is a view showing another arrangement for supplying a substance which reacts with the sample S into the solution around the sample.
Figure 15:
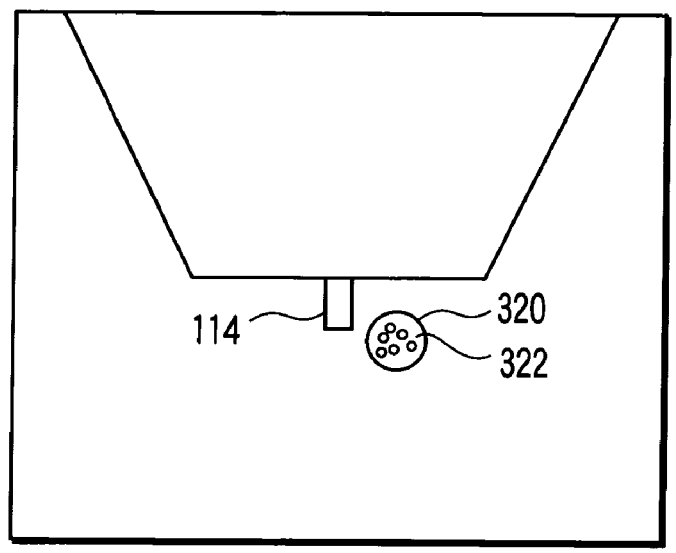
FIG. 15 is a view showing a monitor image including the application spot of trap light and cage-photolytic light and the cantilever in the arrangement shown in FIG. 14.

FIG. 14 shows another arrangement for supplying a substance which reacts with the sample S into liquid around the sample. In this arrangement, caged compounds are added to the surfaces of nanoparticles such as gold colloid, the nanoparticles are collected at a position near the probe by using a laser trap, and the caged compounds are released by the application of cage-photolytic light.

As shown in FIG. 14, a dichroic mirror 330 which transmits the cage-photolytic light Lc and reflects trap light Lt is placed below the dichroic mirror 105. Note that the dichroic mirror 105 transmits the trap light Lt as well as the cage-photolytic light Lc.

With this arrangement, the cage-photolytic light Lc and trap light Lt are combined with each other by the dichroic mirror 330, and the resultant light is applied into the liquid near the cantilever 114 through the dichroic mirror 105 and objective lens 115. Therefore, the trap light Lt and cage-photolytic light Lc are applied at the same position.

In this manner, nanoparticles 322 such as gold colloid having caged compounds added to their surfaces are introduced in the solution 227 in advance. The trap light Lt and UV light Lc for cage release are applied into the solution 227 at the same focusing position near the probe 114a of the cantilever 114. In accordance with the application of the trap light Lt, the nanoparticles 322 in the solution 227 gather in a spot 320 of the trap light Lt. Since the cage-photolytic light Lc is also applied to the spot 320 of the trap light Lt, the caged compounds added to the surfaces of the nanoparticles 322 gathering in the spot 320 are released.

As a method of aligning the cage-photolytic light Lc with the position of each colloid particle, a method of limiting a visual field position can be used as well as a method of changing the angle of an optical axis. This method can be performed by using a stop, deformable mirror, or the like.

Figure 16:
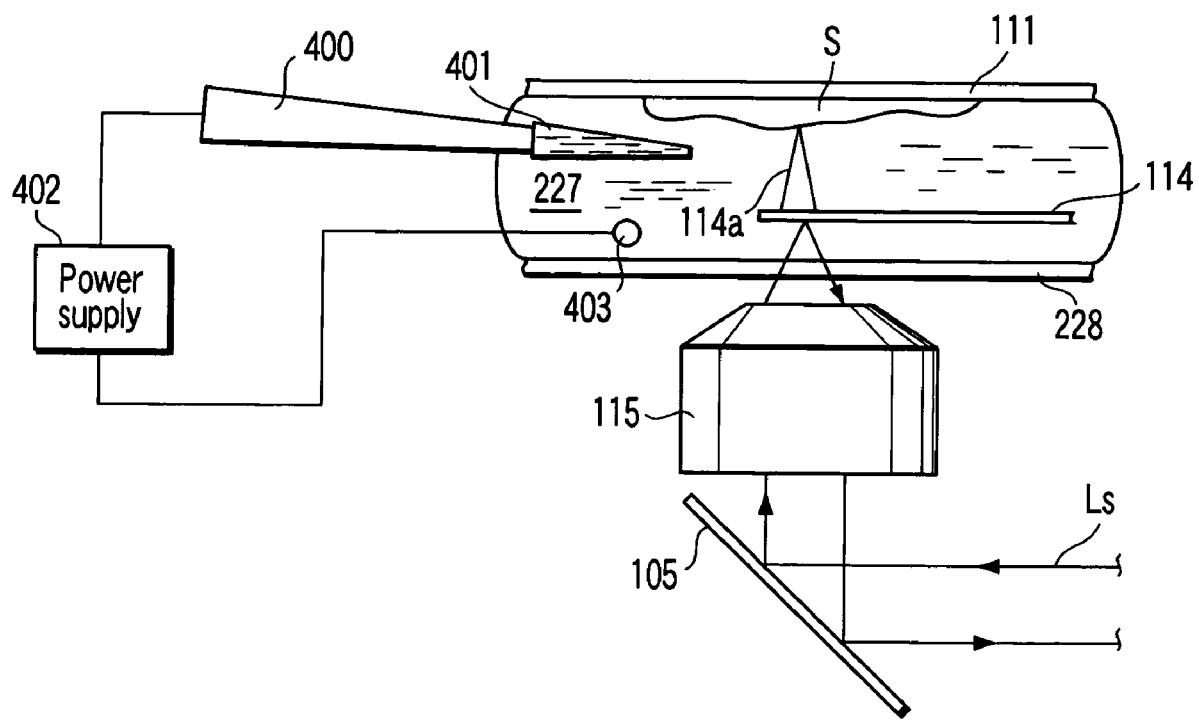
FIG. 16 is a view showing another arrangement for supplying a substance which reacts with the sample S into the solution around the sample.

FIG. 16 shows another arrangement for supplying a charged molecule which reacts with the sample S into a solution around the sample. In this arrangement, a conductive needle is used in place of a capillary.

As shown in FIG. 16, first of all, a charged molecule 401 which reacts with the sample S is made to adhere to the tip of a conductive needle 400. The tip of the needle 400 to which the charged molecule 401 adheres is placed in the solution 227. A counter electrode 403 is also placed in the solution 227 in advance.

When a power supply 402 applies a predetermined voltage between the needle 400 and the counter electrode 403, the charged molecule 401 adhering to the tip of the conductive needle 400 is released from the tip of the needle 400 into the solution 227 to cause a biochemical change in the sample S.

Referring to FIG. 16, the tip of the needle 400 is placed in the solution 227. If, however, the sample S is a cell, the tip may be inserted into the cell. In this case, the position where the charged molecule 401 is to be released can be limited to the inside of the cell. Referring to FIG. 16, the charged molecule is made to adhere to the conductive needle 400. A cantilever which is made of a conductive material or has a conductive surface is also commercially available. Therefore, a charged molecule may be made in advance to adhere to the surface of the cantilever which does come into direct contact with the sample S, and a potential can be set between the counter electrode 403 and the cantilever 114. In this case, there is no need to use any holding mechanism/positioning mechanism for inserting the needle 400. In addition, the charged molecule can be released at a shorter distance from the probe 114a, i.e., the sample S.

Although the embodiments of the present invention have been described with reference to the views of the accompanying drawing, the present invention is not limited to these embodiments and can be variously modified and changed within the spirit and scope of the invention.

The method of applying a stimulus or action to a sample within a temporally or spatially limited range is not limited to the cage release method, and there is available a method of discharging only a small amount of agent or using charged particles. Any form can be employed as long as a similar action state can be recreated by a reaction occurring in a living organism in experiments.

According to the present invention, there are provided a scanning probe microscope and molecular structure change observation method which allow real-time observation of a morphological change due to the biochemical reaction of a living molecule such as a living tissue, cell, or protein molecule. This makes it possible to observe/measure a morphological change in a living molecule as a direct result from its biochemical reaction separately from other conditions.

What is claimed is:

1. A molecular structure change observation method comprising:
    applying photolytic light to a caged compound existing in liquid or a sample while scanning the sample in the liquid with a cantilever; and
    controlling a distance between the sample and a probe provided at an end portion of the cantilever in accordance with a timing of an application of the photolytic light so as to reduce an influence of the photolytic light on the cantilever when applying the photolytic light.

2. A molecular structure change observation method according to claim 1, wherein the photolytic light releases a protecting group of the caged compound and is ultraviolet light.

3. A molecular structure change observation method according to claim 1 or 2, further comprising observing at least one of the sample, the cantilever and the probe.

4. A molecular structure change observation method according to claim 1 or 2, further comprising controlling an application time of the photolytic light.

5. A scanning probe microscope comprising:
    a cantilever;
    a scanning mechanism which relatively scans the cantilever and a sample which exist in liquid;
    an application mechanism which applies photolytic light to a caged compound existing in the liquid or the sample during the scanning; and
    a control mechanism which controls a distance between the sample and a probe provided at an end portion of the cantilever in accordance with a timing of an application of the photolytic light so as to reduce an influence of the photolytic light on the cantilever.

6. A scanning probe microscope according to claim 5, further comprising a detection mechanism which optically detects a displacement of the cantilever due to an interaction between the cantilever and the sample, and an optical mechanism which separates detection light used for the detection mechanism and the photolytic light applied to the caged compound.

7. A scanning probe microscope according to claim 6, further comprising an optical device which prevents the photolytic light from reaching the detection mechanism.

8. A scanning probe microscope according to any one of claims 5 to 7, wherein the photolytic light is ultraviolet light.

9. A scanning probe microscope according to any one of claims 5 to 7, wherein the cantilever or the probe is functionalized with a functional group or a molecule.

10. A scanning probe microscope comprising:
    a cantilever;
    a scanning mechanism which relatively scans the cantilever and a sample which exist in liquid;
    a detection mechanism which optically detects a displacement of the cantilever due to an interaction between the cantilever and the sample;
    an application mechanism which applies photolytic light to a caged compound existing in the liquid during the scanning;
    a control mechanism which controls a distance between the sample and a probe provided at an end portion of the cantilever in accordance with a timing of an application of the photolytic light so as to reduce an influence of the photolytic light on the cantilever;
    an optical device which prevents the photolytic light from reaching a light detection element of the detection mechanism; and
    an optical microscope which observes at least one of the sample, the cantilever and the probe.

11. A scanning probe microscope according to claim 10, wherein the photolytic light is applied to part or all of a visual field of the optical microscope through an objective lens of the optical microscope.

12. A scanning probe microscope according to claim 10 or 11, wherein the photolytic light is ultraviolet light.

13. A scanning probe microscope according to claim 10 or 11, further comprising a control unit which controls an application time of the photolytic light.

14. A scanning probe microscope comprising:
    a cantilever;
    a scanning mechanism which relatively scans the cantilever and a sample which exist in liquid;
    an action mechanism which acts into the liquid or the sample within a temporally or spatially limited range during the scanning; and
    a control mechanism which controls a distance between the sample and a probe provided at an end portion of the cantilever in accordance with a timing of an action of the action mechanism so as to reduce an influence of the action mechanism on the cantilever.

15. A scanning probe microscope comprising:
    a cantilever;
    a scanning mechanism which relatively scans the cantilever and a sample which exist in liquid;

a mechanism which applies light or an action to cause a change of a molecule existing in the liquid or the sample during the scanning; and a control mechanism which controls a distance between the sample and a probe provided at an end portion of the cantilever in accordance with a timing of an application of the light or the action so as to reduce an influence of the application of the light or the action on the cantilever, wherein the control mechanism retracts the cantilever or the sample in a direction to separate from each other when the light or the action is applied.

16. A molecular structure change observation method comprising steps of:

relatively scanning a cantilever and a sample which exist in liquid;

applying light or an action to cause a change of a molecule existing in the liquid or the sample during the scanning; and retracting the cantilever or the sample in a direction to separate from each other in accordance with a timing of an application of the light or the action so as to reduce an influence of the application of the light or the action on the cantilever when the light or the action is applied.

17. A molecular structure change observation method comprising steps of:

relatively scanning a cantilever and a sample which exist in liquid;

applying light or an action into the liquid or the sample within a temporally or spatially limited range during the scanning; and retracting the cantilever or the sample in a direction to separate from each other in accordance with a timing of an application of the light or the action so as to reduce an influence of the application of the light or the action on the cantilever when the light or the action is applied.

* * * * *